United States Patent
Lochard et al.

(10) Patent No.: US 8,716,342 B2
(45) Date of Patent: *May 6, 2014

(54) METHOD FOR PREPARING MOLECULAR COMPLEXES BETWEEN ADAPALENE AND CYCLODEXTRINS

(75) Inventors: Hubert Lochard, Brens (FR); Bernard Freiss, Castres (FR)

(73) Assignee: Galderma Research & Development, Biot (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/259,945

(22) PCT Filed: Apr. 9, 2010

(86) PCT No.: PCT/FR2010/050682

§ 371 (c)(1),
(2), (4) Date: Dec. 8, 2011

(87) PCT Pub. No.: WO2010/116099

PCT Pub. Date: Oct. 14, 2010

(65) Prior Publication Data

US 2012/0077970 A1    Mar. 29, 2012

(30) Foreign Application Priority Data

Apr. 9, 2009   (FR) ...................................... 09 52345

(51) Int. Cl.
*A61K 31/192*   (2006.01)
*A61K 47/40*   (2006.01)

(52) U.S. Cl.
USPC ........................................... 514/569; 514/58

(58) Field of Classification Search
USPC ..................................................... 514/58, 569
See application file for complete search history.

(56) References Cited

U.S. PATENT DOCUMENTS

| 4,717,720 | A | | 1/1988 | Shroot et al. |
| 5,196,575 | A | * | 3/1993 | Sebastian ...................... 562/402 |
| 2005/0274671 | A1 | | 12/2005 | Fages et al. |
| 2006/0246140 | A1 | | 11/2006 | Lochard et al. |
| 2008/0008727 | A1 | | 1/2008 | Fredon et al. |

FOREIGN PATENT DOCUMENTS

| EP | 0 199 636 A1 | 10/1986 |
| WO | WO 03/043604 A1 | 5/2003 |
| WO | WO 2004/096284 A1 | 11/2004 |
| WO | WO 2006/042858 A2 | 4/2006 |
| WO | WO 2006/070093 A1 | 7/2006 |

OTHER PUBLICATIONS

Definition of can, Free Merriam-Webster Dictionary, http://www.merriam-webster.com/dictionary/can, accessed online on Jun. 10, 2013.*

International Search Report (PCT/ISA/210) issued on Sep. 3, 2010, by French Patent Office as the International Searching Authority for International Application No. PCT/FR2010/050682.

* cited by examiner

*Primary Examiner* — Shaojia Anna Jiang
*Assistant Examiner* — Jonathan S Lau
(74) *Attorney, Agent, or Firm* — Dentons US LLP

(57) ABSTRACT

A method for preparing molecular complexes between Adapalene and cyclodextrins using the technology of dense fluids under pressure, especially that of CO2 is described.

21 Claims, 2 Drawing Sheets

METHOD FOR PREPARING MOLECULAR COMPLEXES BETWEEN ADAPALENE AND CYCLODEXTRINS

This application is the U.S. national phase of PCT/FR2010/050682, filed Apr. 9, 2010, and designating the U.S. (published in the French Language on Oct. 14, 2010, as WO 2010/116099 A1; the title and abstract were also published in English), which claims priority under 35 U.S.C. §119 FR 0952345, filed Apr. 9, 2009, each hereby expressly incorporated by reference in its entirety and each assigned to the assignee hereof.

The present invention resides in the field of chemistry and pharmacy and relates to a method for preparing soluble molecular complexes using the technology of dense fluids under pressure, especially that of $CO_2$. In particular, the present invention relates to a method for preparing molecular complexes between Adapalene and cyclodextrins using the technology of dense fluids under pressure.

New pharmaceutical molecules, with a high added value, are in 40% of cases water-soluble or of low water-solubility, which is detrimental to their bioavailability.

In the pharmaceutical, cosmetics and nutraceutical fields, there are a certain number of patent applications, patents and publications relating to the formation, in a medium under pressure, of molecular complexes of an active substance in a coating substrate. Nevertheless, most of the methods described do not relate to the objective of improving the bioavailability, but rather to the adsorption of an active substance onto a substrate.

Van Hees et al. (Application of supercritical carbon dioxide for tAze preparation of a Piroxicam-ss-cyclodextrin inclusion compound, Pharmaceutical Research, vol. 16, N 12, 1999) describe in their publication a method for the inclusion of Piroxicam in (3-cyclodextrins using supercritical $CO_2$. Since piroxicam is of low solubility in water, its inclusion in P-cyclodextrins should make it possible to increase its water-solubility. The method consists in placing a mixture of piroxicam and (3-cyclodextrins in a reactor, left in the static mode. After depressurization, the mixture obtained is ground and homogenized before characterization by: DSC (Differential Scanning calorimetry), measurement of solubility in acetonitrile and comparison with the solubility of piroxicam alone, and spectroscopic methods.

The DSC analysis makes it possible to draw conclusions regarding the complexation of the piroxicam with the p-cyclodextrin.

Application WO2006/070093 describes a composition comprising adapalene solubilized in an aqueous medium with cyclodextrins or derivatives thereof. The composition therefore comprises a physical mixture between the adapalene and the cyclodextrins.

Application WO2004/096284 describes a method for preparing soluble molecular complexes comprising one or more active substances of low solubility in an aqueous medium, included in one or more host molecules, and in particular analgesics, antipyretics, antibiotics and anti-inflammatories. Said method comprises a step (a) of bringing one or more active substances into contact with one or more host molecules, a step (b) of carrying out a molecular diffusion step by bringing a dense fluid under pressure into contact, in static mode, with the mixture obtained in step (a), in the presence of one or more diffusion agents, and a step (c) of recovering the molecular complex thus formed.

Surprisingly, the inventors of the present invention have discovered that a method comprising a step of molecular diffusion using a dense fluid under pressure in static mode, and devoid of the subsequent washing step using a supercritical fluid, significantly improves the degree of inclusion of the active substance, and in particular according to the amount of a diffusion agent added to the medium.

Indeed, as demonstrated in the examples, this method makes it possible to obtain a molecular complex comprising Adapalene and cyclodextrins, the solubility of which is greatly improved compared with the physical mixture with Adapalene and cyclodextrins.

Thus, the present invention relates to a method for preparing soluble molecular complexes comprising an active substance of low solubility in an aqueous medium, and in particular Adapalene included in one or more host molecules, characterized in that it is limitingly made up of the following steps:

(a) bringing one or more active substances into contact with one or more host molecules, (b) carrying out a step of molecular diffusion by bringing a dense fluid under pressure into contact, in static mode, with the mixture obtained in step (a), in the presence of one or more diffusion agents, and (c) recovering the molecular complex thus formed.

The method described above may comprise an additional step d) of drying the complex, advantageously at a temperature of between 40° C. and 60° C., preferably under vacuum.

The present invention relates to a method for preparing molecular complexes between Adapalene and cyclodextrins using the technology of dense fluids under pressure.

For the purpose of the present invention, the term "dense fluid under pressure" is intended to mean any fluid used at a temperature or a pressure above the critical value thereof. Advantageously, it is pure $CO_2$ or $CO_2$ as a mixture with an organic solvent conventionally used by those skilled in the art.

For the purpose of the present invention, the expression "active substance of low solubility in an aqueous medium" is intended to mean any active substance which is of low solubility or insoluble in an aqueous medium and which has in particular a solubility of less than at least 20 mg/ml.

By virtue of its ability to bind RAR and/or RXR receptors, adapalene is described in patent application EP 0 199 636 as a compound from the family of benzonaphthalene retinoids known as 6-(3-(1-adamantyl)-4-methoxyphenyl)-2-naphthoic acid (adapalene) and the methyl ester thereof.

In particular, adapalene and also the salts thereof will be preferred.

The term "adapalene salts" is intended to mean the salts formed with a pharmaceutically acceptable base, in particular inorganic bases such as sodium hydroxide, potassium hydroxide and aqueous ammonia, or organic bases such as lysine, arginine or N-methylglucamine.

The term "adapalene salts" is also intended to mean the salts formed with fatty amines such as dioctylamine and stearylamine.

The preferred concentrations of Adapalene are between 0.0001 and 20% by weight, relative to the total weight of the composition.

Preferably, the composition according to the invention comprises between 0.001 and 5% and advantageously between 0.01 and 1% by weight of adapalene, relative to the total weight of the composition, preferentially between 0.01 and 0.5%, preferably between 0.1 and 0.4% by weight of adapalene, even more preferentially 0.3% by weight of adapalene.

For the purpose of the present invention, the term "host molecule" is intended to mean any substance capable of capturing active substances. Advantageously, the host molecule is chosen from the group made up of polysaccharides and monosaccharides, in particular cyclodextrins and mixtures thereof.

The cyclodextrins used in the present invention are those known in the literature.

Cyclodextrins (CDs) are cyclic oligosaccharides consisting of ($\alpha$-1,4) $\alpha$-D-glucopyranose units with a lipophilic central cavity and a hydrophilic external surface (Frömming K H, Szejtli J: "Cyclodextrins in pharmacy", Kluwer Academic Publishers, Dortrecht, 1994).

Cyclodextrins are known to increase the solubility of molecules by the formation of a "cage"-like structure which has an external hydrophilic part and an internal hydrophobic part. Cyclodextrins can thus form inclusion complexes with many medicaments by accepting, inside the cavity, the whole molecule or, more commonly, the lipophilic part of the molecule.

The most abundant natural cyclodextrins are the $\alpha$-cyclodextrins, the $\beta$-cyclodextrins and the $\gamma$-cyclodextrins.

The $\alpha$-cyclodextrins (also known as Schardinger's $\alpha$-dextrin, cyclomaltohexaose, cyclohexaglucan, cyclohexaamylose, $\alpha$-CD, ACD, C6A) comprise 6 glucopyranose units. The $\beta$-cyclodextrins (also known as Schardinger's $\beta$-dextrin, cyclomaltoheptaose, cycloheptaglucan, cycloheptaamylose, $\beta$-CD, BCD, C7A) comprise 7 glucopyranose units, and the $\gamma$-cyclodextrins (also known as Schardinger's $\gamma$-dextrin, cyclomaltooctaose, cyclooctaglucan, cyclooctaamylose, $\gamma$-CD, GCD, C8A) comprise 8 glucopyranose units.

Among these three types of CDs, the $\beta$-cyclodextrins appear to be the most useful complexing pharmaceutical agents owing to the size of their cavity, to their availability, to their properties and to their low costs.

According to Dr J. Szejtli ("Cyclodextrins", in Encyclopedia of Supramolecular Chemistry, publisher Marcel Dekker, 2004), cyclodextrins are advantageous but also exhibit limiting factors which restrict the application of cyclodextrins to certain types of pharmaceutical products. Moreover, not all products are suitable for complexation with cyclodextrins. Many products cannot be complexed or else the complexation provides no essential advantage. Inorganic compounds are generally unsuitable for complexation with cyclodextrins.

Cyclodextrin derivatives can also be used in the present invention. In cyclodextrins, each glucopyranose unit has three free hydroxyl groups which differ in terms of their function and their reactivity.

Advantageously, it is a question of alpha-cyclodextrin, beta-cyclodextrin, gamma-cyclodextrin and also cyclodextrin derivatives such as methyl-$\beta$-cyclodextrin, hydroxypropyl-beta-cyclodextrin or sulfobutylcyclodextrin.

In one preferred embodiment of the invention, methyl-$\beta$-cyclodextrin will be chosen, in particular the one known as CRISMEB and preferentially the randomized methyl-$\beta$-cyclodextrin known as RAMEB.

The molar ratio between the active agent and the cyclodextrin(s) is of the order of 1:1 to 1:10. In one preferred embodiment, the molar ratio is 1:2 or 1:4 or 1:6 or 1:8 else 1:10.

For the purpose of the present invention, the term "diffusion agent" is intended to mean any solvent which promotes an interaction of the active substance with the host molecule.

Advantageously, this diffusion agent is chosen from the group made up of alcohols, ketones, ethers, esters and water with or without surfactant, and mixtures thereof. Even more advantageously, it is water.

For the purpose of the present invention, the term "static mode" is intended to mean a reaction or a method in which all the reactants are simultaneously brought together and where the reaction is left to take place. For example, in step (b) of the present invention, the active substance(s), water and supercritical $CO_2$ are placed in an autoclave and left to react for several hours. The product mass does not change during the reaction. Conversely, in the dynamic mode, the reactants are provided as and when the reaction or the production evolves.

In the case of a dynamic mode, there is often circulation of a fluid or stirring. The product mass changes during the production.

The active substance and the host molecule are introduced in solid or liquid form into a container into which the dense fluid under pressure and the diffusion agent are injected in judicially selected proportions. The pressure and temperature conditions and also the duration of the treatment are defined, by any suitable method, according to the nature of the active substance(s) and of the host molecule(s).

Advantageously, the molecular diffusion step (b) of the method according to the present invention is carried out with stirring.

The diffusion agent can be added continuously or batchwise in an amount of between 1 and 25% by weight, preferably between 8 and 20% by weight. Preferentially, for natural cyclodextrins, the amount is between 10 and 15%; between 8 and 15% for cyclodextrins of RAMEB or HBCD type; between 12 and 15% for cyclodextrin derivatives.

The time necessary for the molecular diffusion in step (b) is determined by any suitable method. This step (b) can be repeated as many times as desired in order to obtain a satisfactory rate of dissolution. Advantageously, step (b) lasts between approximately 2 and 16 hours.

The pressure and temperature conditions of step (b) are chosen so as to promote the molecular diffusion. Advantageously, the pressure of the supercritical fluid is between 5 MPa and 40 MPa and the temperature between 0° C. and 120° C. In one preferred embodiment of the invention, the temperature conditions of step b) are between 60° C. and 90° C. and preferentially between 60° C. and 85° C.

Advantageously, step (b) of the method according to the present invention is carried out in a closed reactor at high pressure.

In one alternative embodiment of the present invention, the method comprises an additional step (b') in which the cyclodextrin(s) is (are) added in excess. In one preferred embodiment, the excess cyclodextrin(s) is added so as to obtain, at the end of the method, a total concentration of cyclodextrin(s) of the order of 24 g/l to 98 g/l and preferably between 60 g/l and 85 g/l.

The method can be carried out batchwise or as described in patent application WO03/043604, included in the present application by way of reference. Advantageously, the method according to the present invention is carried out batchwise.

The present invention also relates to the soluble molecular complexes comprising at least one active substance of low solubility in an aqueous medium, of Adapalene type, included in one or more host molecules, characterized in that they can be obtained by the method according to the present invention.

The implementation of the step of molecular diffusion in a dense medium under pressure in the presence of a diffusion agent allows a strong interaction of the particles of active substance with the host molecule, thereby promoting the dissolution in an aqueous medium, which is multiplied by approximately 100 by the method according to the invention.

The invention also relates to the use of the complexes obtained by means of the method, for treatment. In particular, given the marked activity of Adapalene in the fields of cell differentiation and proliferation, the complexes of the invention are particularly suitable in the following therapeutic fields:

1) for treating dermatological conditions associated with a keratinization disorder relating to differentiation and proliferation, in particular for treating common acne, comedonal acne, polymorphic acne, acne rosacea, nodulocystic acne, acne conglobata, senile acne, secondary acne such as solar acne, acne medicamentosa or occupational acne, hidradenitis suppurativa, 2) for treating other types of keratinization disorders, in particular ichthyosis, ichthyosiform conditions, Darier's disease, palmoplantar keratodermia, leucoplasia and leucoplasiform conditions, and cutaneous or mucosal (oral) lichen, 3) for treating other dermatological conditions associated with a keratinization disorder with an inflammatory and/or immunoallergic component, and in particular all forms of psoriasis, whether cutaneous, mucosal or ungula, and even psoriatic arthritis, or else cutaneous atopy, such as eczema, or respiratory atopy or else gingival hypertrophy; the compounds can also be used in certain inflammatory conditions which do not exhibit a keratinization disorder, such as folliculitis, 4) for treating all dermal or epidermal proliferations, whether benign or malignant, whether or not of viral origin, such as common warts, flat warts, molluscum contagiosum, and epidermodysplasia verruciformis, oral or florid papillomatoses and proliferations that may be induced by ultraviolet radiation, in particular in the case of actinic keratoses, 5) for repairing or combating skin aging, whether photo-induced or chronological, or for reducing pigmentations, or any pathological conditions associated with chronological or actinic aging, 6) for preventatively or curatively treating cicatrization disorders, skin ulcers, for preventing or for repairing stretch marks, or else for promoting cicatrization, 7) for combating sebaceous function disorders, such as hyperseborrhea of acne or simple seborrhea, 8) in the treatment of any skin condition of the fungal origin, such as tinea pedis and tinea versicolor, 9) in the treatment of dermatological conditions with an immunological component, 10) in the treatment of skin disorders caused by exposure to UV radiation, and 11) in the treatment of dermatological conditions associated with an inflammation or an infection of the tissues surrounding the hair follicle, in particular caused by microbial colonization or infection, in particular impetigo, seborrheic dermatitis, folliculitis or sycosis barbae, or involving any other bacterial or fungal agent.

Preferably, the complexes according to the invention are particularly suitable for the preventative or curative treatment of common acne.

Figure 1:
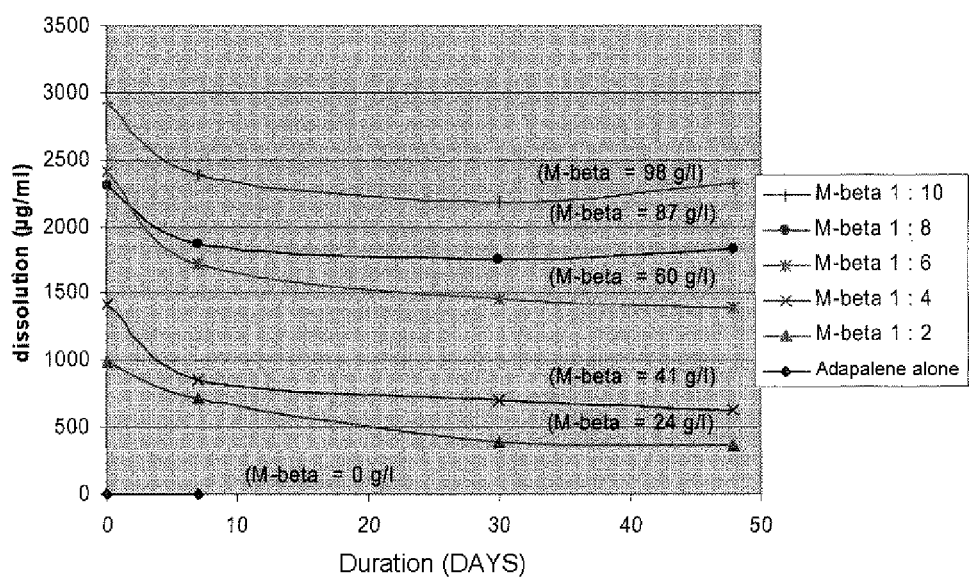
FIG. 1: Adapalene/M-beta cyclodextrin dissolution profile, Matured mixture.

The following examples of implementation of the method are given by way of nonlimiting indication.

EXAMPLE 1

Obtaining a Complex Comprising Adapalene (Active Substance) and Various Types of Cyclodextrins (Host Molecule)

The objective of this example is to verify the complexation of adapalene with cyclodextrins using supercritical $CO_2$ in order to increase the aqueous solubility of the active ingredient.

The complexation yield is evaluated by measuring the reduction (or disappearance) of the thermal peak relative to the active ingredient which has remained free.

Materials Used

Table I below lists all the materials used during this study.

|  | M (g/mol) | Water g % g | Batch No. |
|---|---|---|---|
| Adapalene | 412.52 | / | RM000144K1263 |
| Alpha-cyclodextrin | 972 | 9% | 60P304 |
| CRISMEB cyclodextrin | 1190 | 2.6% | E001 LAB 3487 |
| M-beta-cyclodextrin N = 7 * 1.8 | 1311.4 | 1.00% | 71P018 |
| Sterile distilled water | 18 | / | MP 7005 |

Operating Conditions

The operating conditions are fixed by default:
One mole of adapalene with the equivalent of several moles of cyclodextrins.
Addition of water so as to reach a content of 20% for natural cyclodextrins, 10% for grafted cyclodextrins.
Maturation for 2 hours at 60° C. and 150 bar.
Drying at 50° C. under vacuum overnight.

Analytical Methods

The content of active ingredient and the dissolution kinetics were carried out according to the methods described hereinafter.

a) Assaying Method

HPLC Chromatographic Conditions
Column: Symmetry C18 250×4.6 mm 5 μm
Mobile phase: 430 volumes of acetonitrile
360 volumes of tetrahydrofuran
210 of water
0.2 volume of trifluoroacetic acid
HPLC apparatus: WATERS 2690/2487
flow rate: 1 ml/min
Wavelength: 270 nm
Detector sensitivity: 2 AUFS
Injected volume: 10 μl
Oven temperature: 25° C.
Analysis time: 15 minutes Preparation of Solutions:

Solutions to be Examined:
The equivalent of 200 mg of Adapalene, exactly weighed out, are introduced into a 25 ml flask. Dissolution is carried out with HPLC dimethylformamide (DMF) and the solution is made up to volume with HPLC dimethylformamide (DMF). 1.0 ml of solution is removed into a 20 ml flask. 5 ml of DMF are added and the mixture is made up to volume with the mobile phase.

Control Solution:
SM: 100 mg of control Adapalene are introduced into a 100 ml flask. Dissolution is carried out with tetrahydrofuran (THF) and the solution is made up to volume with tetrahydrofuran (THF).

Range C1: Dilution of SM to 1/1000th in the mobile phase (0.001 mg/ml).
C2: Dilution of SM to 1/100th in the mobile phase (0.010 mg/ml).
C3: Dilution of SM to 1/50th in the mobile phase (0.020 mg/ml).
C4: Dilution of SM to 1/20th in the mobile phase (0.050 mg/ml).
C5: Dilution of SM to 1/10th in the mobile phase (0.100 mg/ml).

Implementation of the Test:

10 µl of each control solution are injected.

A linear regression of the surface areas of the Adapalene peaks relative to the concentrations is performed. The correlation coefficient should be greater than 0.995.

2 preparations are carried out per test.

20 µl of the solution to be examined are injected. The area of the Adapalene peak in each solution to be examined is measured. The concentration X in mg/ml is deduced therefrom according to the regression line of the controls.

The Adapalene content expressed as a percentage (w/w) is given by the formula:

$$[\text{Adapalene}] \text{ as a percentage (w/w)} = X \times 500 \times 100/Ts$$

Ts: Test sample in mg of the substance to be examined.
b) Kinetics of Dissolution at 3 g/l and at 25° C.

The chromatographic conditions and the concentrations of the control solutions are the same as those of the assay.

Equipment:
Stirring: 15-position bench
Thermostated bath: 25° C. +/−2° C. verified on Prolabo PR 531 probe
HPLC Waters 2690-Detector 2487/2996
Weighing out: Sartorius A200 balance
Dilutions: Eppendorf Research 1000, Eppendorf Research 5000, Gilson M1000 micropipette
Ultrapure water station: ELGA Operating conditions:

A test sample equivalent to 150 mg of Adapalene is introduced into a 100 ml Erlenmeyer flask. 50 ml of water are added. The mixture is stirred magnetically at 400 rpm or position 4 in a waterbath at 25° C. +/−2° C. A 2 ml sample is withdrawn at 15, 30, 60, 120 and 1140 minutes, while stirring magnetically. These withdrawn samples are filtered through 0.45 µm Gelman GHP Acrodisc polypropylene filters. The solution must be clear. The withdrawn samples are diluted by a factor "a" in the mobile phase, making it possible to have an Adapalene peak of surface area included between the surface areas of Control 1 and Control 5.

Implementation of the Test

10 µl of each control solution are injected. A linear regression of the surface areas of the Adapalene peaks relative to the concentrations is performed.

The correlation coefficient should be greater than 0.995.

10 µl of the solution to be examined are injected.

The area of the Adapalene peak in each solution to be examined is measured.

The concentration X in µg/ml is deduced therefrom according to the regression line of the controls.

The concentration in µg of Adapalene solubilized per ml is calculated with the formula:

$$[\text{Adapalene}] \text{ in } \mu g/ml = X \times a$$

The variation in the amount dissolved in µg/ml as a function of time is represented on a graph.

At the end of dissolution, the appearance is immediately noted and the pH of the solution immediately measured.

Results and Course of the Study

In order to verify the apparent solubility of adapalene in aqueous media, three tests were carried out with various cyclodextrins and using ethanol as diffusion agent:
alpha-cyclodextrin (6 glucose units)
methyl-beta-cyclodextrin CRISMEB
methyl-beta-cyclodextrin RAMEB/ethanol These samples were analyzed and the results are collated in table II below, in which the following are indicated:
The various "cyclodextrin/molar ratio" systems,
The reference sample,
The content by weight of active ingredient after maturation,
The results of aqueous dissolution, at 15, 30, 60 and 120 minutes, of adapalene after maturation (bold) and for a corresponding physical mixture (italics).
The pH of the dissolution medium after 120 minutes for the powder after maturation (bold) and for the corresponding physical mixture (italics).

TABLE II

| | | | Without maturation | | | | | With maturation | | | | |
|---|---|---|---|---|---|---|---|---|---|---|---|---|
| | cyclo/ratio | % Al | 15' | 30' | 60' | 120' | pH | 15' | 30' | 60' | 120' | pH |
| TNT-9A | alpha 1:2 | 15.9 | *0* | *0* | *0* | *0* | *6* | 0 | 0 | 0 | 0 | 6 |
| TNT-9B | CRISMEB 1:2 | 10.1 | *1* | *1* | *2* | *2* | *5* | 6 | 5 | 5 | 4 | 5 |
| TNT-9C | RAMEB EtOh 1:2:1 | 13.2 | *1* | *2* | *2* | *3* | *5* | 382 | 400 | 376 | 346 | 4 |

This example shows the complexation of adapalene with at least 2 types of cyclodextrins and it shows a highly improved solubility in the case of the complexation of adapalene with methyl-beta-cyclodextrin (RAMEB type).

EXAMPLE 2

Stabilization of the Complex Comprising Adapalene and Methyl-Beta-Cyclodextrin

The objective of this example is to show the stability of the complex obtained in example 1 by varying the molar ratio and temperature parameters of the method while studying the dissolution profile of the complex.

In order to confirm the advantage of increasing the concentration of cyclodextrin and to differentiate between the effect of the cyclodextrins complexed during maturation and the effect of the cyclodextrins added to the dissolution medium, complexes of various ratios were prepared using supercritical $CO_2$ (molar ratio 1:2; 1:4; 1:6; 1:8; 1:10).

Moreover, for this test series, the maturation temperature was 85° C. instead of 60° C. Dissolution kinetics were subsequently performed at 15 minutes, 7 days, 30 days and 48 days (table III).

These values are reported in the form of a graph in FIG. 1. It is noted that increasing the maturation temperature and the cyclodextrin ratio made it possible to obtain a greater apparent solubility, even though the profiles generally remain decreasing.

TABLE III

| Batch No. | Cyclo/ratio | Content by weight | Dissolution (pH) | | | |
|---|---|---|---|---|---|---|
| | | | 15 minutes | 7 days | 30 days | 48 days |
| Adapalene alone | | 100% | 0 µg/ml (5.7) | 0 µg/ml (5.7) | nr | nr |
| TNT-01149 | M-beta/1:2 | 12.5% | 993 µg/ml (3.9) | 720 µg/ml (3.9) | 391 µg/ml (nr) | 370 µg/ml (4.6) |
| TNT-02041 | M-beta/1:4 | 7.3% | 1413 µg/ml (3.9) | 854 µg/ml (3.9) | 704 µg/ml (nr) | 625 µg/ml (4.5) |
| TNT-02042 | M-beta/1:6 | 5.0% | 2406 µg/ml (3.8) | 1723 µg/ml (3.8) | 1456 µg/ml (nr) | 1392 µg/ml (4.0) |
| TNT-02043 | M-beta/1:8 | 3.4% | 2307 µg/ml (3.7) | 1867 µg/ml (3.8) | 1755 µg/ml (nr) | 1829 µg/ml (3.9) |
| TNT-02044 | M-beta/1:10 | 3.1% | 2919 µg/ml (3.8) | 2383 µg/ml (3.8) | 2189 µg/ml (nr) | 2318 µg/ml (3.8) |

Increasing the molar ratio during maturation amounts to increasing the concentration of M-beta cyclodextrin subsequently present in the dissolution medium. In order to clearly dissociate these two effects, dissolution profiles for the ratio of 1:2, 1:4 and 1:6 batches were also performed in a solution containing cyclodextrin in excess in order to maintain a total concentration of cyclodextrin of 80 g/l (FIG. 2).

Figure 2:
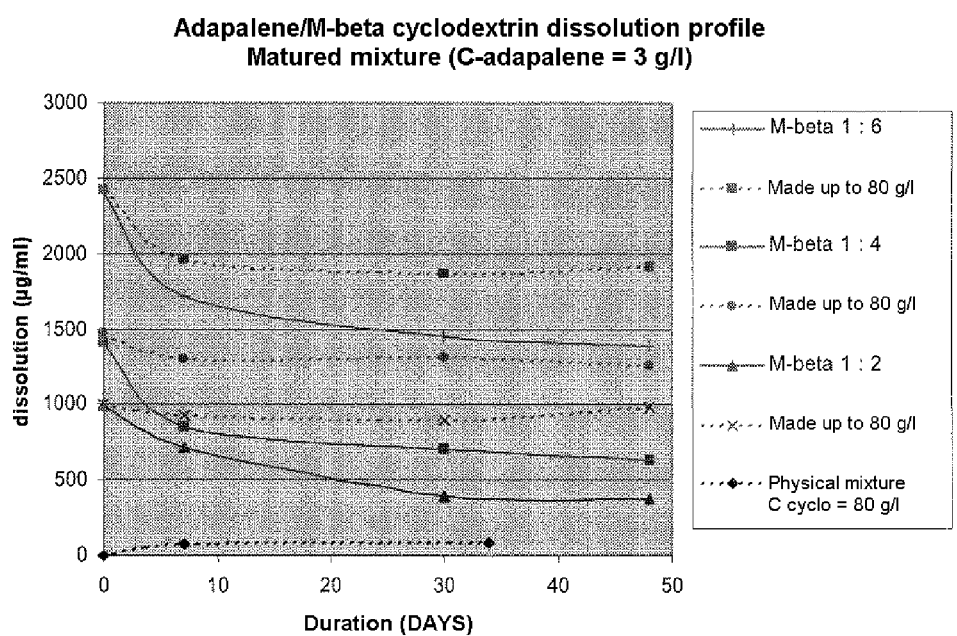
FIG. 2: Adapalene/M-beta cyclodextrin dissolution profile, Matured mixture.

On the graph in FIG. 2, the dashed curves correspond to solutions of which the compositions are strictly identical (C-adapalene=3 g/l, C-cyclodextrin=80 g/l). The numerical values of these curves are indicated in table IV below.

TABLE IV

| Batch No. | Cyclo/ratio | Dissolution (pH) | | | | |
|---|---|---|---|---|---|---|
| | | 15 minutes | 7 days | 30 days | 35 days | 48 days |
| Physical mixture | | 2 µg/ml (5.0) | 80 µg/ml (4.5) | nr | 82 µg/ml (4.6) | nr |
| TNT-01149 | M-beta/1:2 | 1001 µg/ml (4.0) | 934 µg/ml (3.9) | 896 µg/ml (nr) | nr | 979 g/ml (4.12) |
| TNT-02041 | M-beta/1:4 | 1468 µg/ml (3.9) | 1304 µg/ml (3.9) | 1308 µg/ml (nr) | nr | 1257 µg/ml (4.0) |
| TNT-02042 | M-beta/1:6 | 2425 µg/ml (3.8) | 1964 µg/ml (3.7) | 1864 µg/ml (nr) | nr | 1914 µg/ml (3.9)) |

It can be concluded that the cyclodextrin complexed during the maturation contributes to increasing the apparent solubility of the adapalene, while the cyclodextrin simply added to the medium improves the stability of the adapalene solution by maintaining the state of equilibrium toward the complexed form.

The invention claimed is:

1. A method for preparing a soluble molecular complex comprising adapalene or a salt thereof included in randomly methylated β-cyclodextrin (RAMEB), the method comprising the following steps: (a) bringing adapalene into contact with RAMEB to form a mixture, (b) carrying out a molecular diffusion step by bringing a dense fluid under pressure into contact, in static mode, with the mixture obtained in step (a), in the presence of a diffusion agent comprising water to afford an aqueous mixture, and (c) recovering the molecular complex from the aqueous mixture thus formed, said molecular complex having a molar ratio of adapalene to RAMEB of from 1:2 to 1:10; followed by (b') dissolving the molecular complex in water to form an aqueous solution thereof and then adding to said aqueous solution free RAMEB in excess to the amount of RAMEB in the molecular complex, in an amount which stabilizes the molecular complex in the aqueous solution.

2. The method as claimed in claim 1, wherein the method further comprises an additional step (d) following step (c) of drying the complex, optionally at a temperature of between 40° C. and 60° C., optionally under vacuum.

3. The method as claimed in claim 1, wherein the dense fluid under pressure is $CO_2$.

4. The method as claimed in claim 1, wherein the diffusion agent further comprises a member selected from the group consisting of alcohols, ketones, ethers, esters, mixtures thereof and mixtures thereof with water.

5. The method as claimed in claim 1, wherein the diffusion agent is water.

6. The method as claimed in claim 1, wherein the molecular diffusion step (b) is carried out with stirring.

7. The method as claimed in claim 1, wherein the water is added continuously or batchwise in an amount of between 1% and 25% by weight.

8. The method as claimed in claim 1, wherein the pressure of the supercritical fluid is between 5 MPa and 40 MPa and the temperature between 0° C. and 120° C.

9. The method as claimed in claim 7, wherein the water is added in an amount between 8% and 15% by weight.

10. The method as claimed in claim 8, wherein the temperature of the supercritical fluid is between 60° C. and 90° C.

11. The method as claimed in claim 1, wherein the amount of free RAMEB which stabilizes the molecular complex in aqueous solution is sufficient to maintain a total concentration of RAMEB of between 50 g/l and 120 g/l in the aqueous solution.

12. The method as claimed in claim 11, wherein the total concentration of RAMEB is between 70 g/l and 90 g/l in the aqueous solution.

13. The method as claimed in claim 12, wherein the total concentration of RAMEB is about 80 g/l in the aqueous solution.

14. The method as claimed in claim 1, wherein the molar ratio of adapalene to RAMEB is from 1:2 to 1:6.

15. The method as claimed in claim 1, wherein the molar ratio of adapalene to RAMEB is from 1:2 to 1:4.

16. The method as claimed in claim 1, wherein the molar ratio of adapalene to RAMEB is from 1:6 to 1:10.

17. The method as claimed in claim 1, wherein the molar ratio of adapalene to RAMEB is about 1:10.

18. The method as claimed in claim 12, wherein the molar ratio of adapalene to RAMEB is from 1:2 to 1:6.

19. The method as claimed in claim 12, wherein the molar ratio of adapalene to RAMEB is from 1:2 to 1:4.

20. The method as claimed in claim 12, wherein the molar ratio of adapalene to RAMEB is from 1:6 to 1:10.

21. The method as claimed in claim 12, wherein the molar ratio of adapalene to RAMEB is about 1:10.

* * * * *